United States Patent [19]

Pifferi et al.

[11] 4,173,648

[45] Nov. 6, 1979

[54] 3β-HYDROXY-18β-OLEAN-9-EN-30-OIC ACIDS

[75] Inventors: Giorgio Pifferi, Milan; Achille Umani-Ronchi, Ancona; Carlo Farina, Valsolda; Afro Gamba, Milan, all of Italy

[73] Assignee: I.S.F. SpA, Milan, Italy

[21] Appl. No.: 886,145

[22] Filed: Mar. 13, 1978

[30] Foreign Application Priority Data

Mar. 16, 1977 [IT] Italy ............................... 21296 A/77

[51] Int. Cl.² .................. C07C 65/14; C07C 69/02; C07C 69/34
[52] U.S. Cl. .................. 424/294; 260/438.1; 260/501.11; 424/311; 424/313; 424/316; 424/317; 560/194; 560/256; 560/257; 562/403
[58] Field of Search ............. 560/194, 257, 249, 256; 260/514.5, 438.1, 501.11; 562/403; 424/294, 311, 313, 316, 317

[56] References Cited

U.S. PATENT DOCUMENTS 3,984,461  10/1976  Pifferi ................................... 560/194

OTHER PUBLICATIONS

Budziarek et al., J. Chem. Soc., 1951, pp. 3019–3026.
McLean et al., J. Chem. Soc., 1952, pp. 432–437.
Barton et al., J. Chem. Soc., 1952, pp. 78–92.

*Primary Examiner*—Jane S. Myers
*Attorney, Agent, or Firm*—Stevens, Davis, Miller & Mosher

[57] ABSTRACT

3β-Hydroxy-18β-olean-9-en-30-oic acids having antiulcer activity of the formula

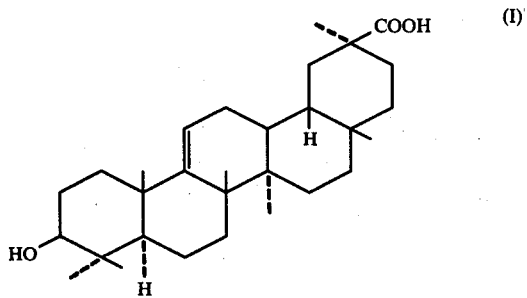

compositions containing the same and process for their preparation.

11 Claims, No Drawings

3β-HYDROXY-18β-OLEAN-9-EN-30-OIC ACIDS

The present invention is concerned with new triterpene derivatives with interesting pharmacological properties and with the preparation thereof.

The new triterpene derivatives according to the present invention are 3β-hydroxy-18β-olean-9-en-30-oic acids of the formula:

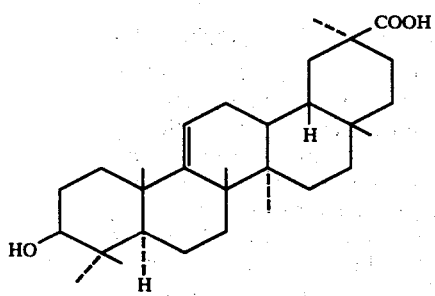
(I)

and corresponding esters in the 3-position with mono- and dicarboxylic acids containing from 2 to 5 carbon atoms, as well as the salts thereof with alkaline metals, amino acids and copper.

Examples of mono- and dicarboxylic acids which can be used to esterify the 3-position in compounds of general formula (I) include acetic, propionic, butyric, malonic, succinic and glutaric acids.

Of the alkali metal salts of the 3-esters and 3-hemiesters of the acid of formula (I), the sodium salt is particularly preferred and of the salts with amino acids, the lysine salt is particularly preferred.

The present invention also provides a process for the preparation of the new compounds, wherein an alkyl ester of the general formula:

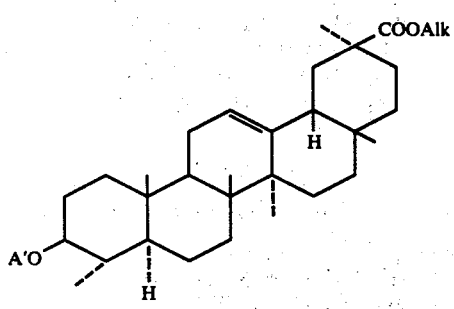
(II)

in which A′ is an acyl radical containing 2 to 4 carbon atoms and Alk is an alkyl radical containing up to 3 carbon atoms, is oxidized to give a keto compound of the general formula:

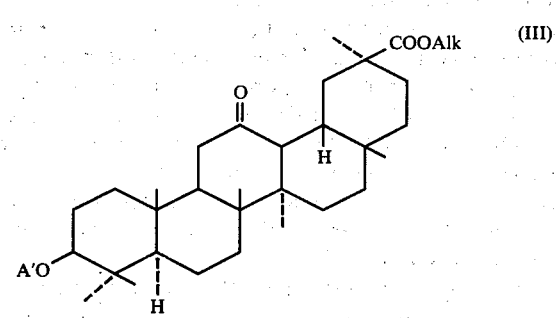
(III)

in which A′ and Alk have the same meanings as above, which is reacted in a solvent with chlorine or bromine under anhydrous conditions to give a compound of the general formula:

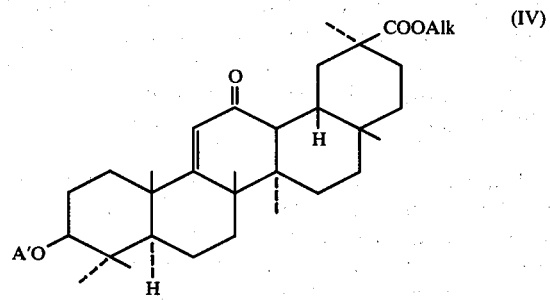
(IV)

in which A′ and Alk have the same meanings as above, and this compound is then reduced to give the compound of the formula (I) which, if desired, is subsequently esterified in the 3-position and/or, if desired, salified to give a corresponding alkali metal, amino acid or copper salt.

Oxidation of (II) can be carried out, for example, with hydrogen peroxide in glacial acetic acid or with m-chloroperbenzoic acid, monoperphthalic acid or perbenzoic acid and a chlorinated solvent, for example chloroform or methylene chloride. Depending upon the oxidizing agent used, the reaction takes place at a temperature of from 24° to 100° C. under anhydrous conditions or in aqueous solution.

The keto compound (III) is then reacted to introduce a double bond in the 9,11-position, this reaction being carried out under anhydrous conditions in the presence of chlorine or bromine in an appropriate solvent, for example, acetic acid, chloroform or methylene chloride.

The unsaturated compound (IV) can then be reduced to the corresponding 12-desoxy compound (I) by reacting it at a temperature about 100° C. under anhydrous conditions in a protic solvent, for example a high boiling point glycol or a saturated alcohol, with hydrazine or a hydrazine derivative and a strong base, for example an alkali metal alcoholate or hydroxide, such as sodium methylate, sodium ethylate, potassium tert.-butylate or sodium or potassium hydroxide.

The compound (I) thus obtained can then, if desired, be esterified in the known manner to give the corresponding 3-0-esters and, if desired, the carboxylic acid group or groups can be salified to give the corresponding alkali metals, amino acid or copper salts.

The compounds of the present invention have a pronounced anti-ulcer action and do not cause sodium retention at the effective dose levels which, together with a low toxicity of active doses, makes them very interesting pharmacologically. The new compounds have been widely studied in tests carried out on animals using, as a comparison compound, carbenoxolone (the disodium salt of glycycrrhetinic acid 3-hemisuccinate) which is a commercially available anti-ulcer compound having a very similar chemical structure to the new compounds of the present invention. The new compounds, when compared with this standard compound, were surprisingly found to possess an interesting anti-ulcer action which was practically dissociated from any undesired sodium retention at the effective dose level.

The pharmacological tests were carried out as described in the following:

ANTI-ULCER ACTION

The test was carried out on male Swiss mice with an average body weight of 23 g. subjected to cold stress by immersion in water and to a contention stress according to the method of C. J. Pfeiffer ("Peptic ulcer", Munksgaard, 1971, page 84). Three dosage levels of 25, 50 and 100 mg/kg and 15 animals for each dosage level were used.

The anti-ulcer action of the compounds was evaluated by calculating the percentage average inhibition, which indicates the inhibition of the ulcer seriousness index in the treated animals, taking 100 as the seriousness index of the controls. The results obtained are given in the following Table I:

TABLE I

| Compound | Dose mg/kg os | % average inhibition | LD$_{50}$ in mice mg/kg per os |
|---|---|---|---|
| Disodium salt of 3β-(3-carboxy-propionoxy-18β-olean-9-en-30-oic acid | 25 | 13 | 1000 |
| | 50 | 22.5 | |
| | 100 | 70.5 | |
| carbenoxolone | 25 | 29.5 | |
| | 50 | 29 | 700 |
| | 100 | 63.5 | |

The present invention also provides pharmaceutical compositions comprising at least one of the new compounds, in admixture with a solid or liquid pharmaceutical diluent or carrier.

ANTI-DIURETIC ACTION

The test was carried out on male Wistar rats with a body weight of 170 g. subjected, according to the method of F. M. Sullivan ("Carbenoxolone in Gastroenterology"—Butterworth, London 1972, page 3), to administration, by means of gastric probe, of 4 ml. of physiological solution, to which the test compound is added, dissolved in 1 ml. distilled water. The urine produced in the five hours after treatment are collected and the potassium and sodium contents are determined. The tests were carried out at two dosage levels, 30 and 60 mg/kg, using, for each dosage level, 8 pairs of animals.

The anti-diuretic activity of the compounds is evaluated by means of the percentage inhibition of the ratio Na$^+$/K$^+$, taking as 100 the ratio observed in the controls.

TABLE II

| Compound | Dose mg/kg | Na$^+$/K$^+$ | % inhibition |
|---|---|---|---|
| Disodium salt of 3β-(3-carboxy-propionoxy-18β-olean-9-en-30-oic acid | 30 | 3.18 | 0 |
| | 60 | 3.59 | −3% |
| carbenoxolone | 30 | 1.81 | 43 |
| | 60 | 1.24 | 64 |

The following Examples are given for the purpose of illustrating the present invention:

EXAMPLE 1

3β-Hydroxy-18β-olean-9-en-30-oic acid 2.5 g. Methyl 3β-acetoxy-18β-olean-12-en-30-oate are dissolved in 200 ml. glacial acetic acid and 7.5 ml. of 120 vol. hydrogen peroxide added thereto. The reaction mixture is kept for 2 hours in a water-bath at 100° C. and then evaporated in vacuo; the solid residue obtained is crystallized from methanol-methylene chloride, 2.2 g. of colorless crystals of methyl 3β-acetoxy-12-oxo-18β-olean-30-oate being obtained; m.p. 299°-301° C.; $[α]_D^{25}$+28.4° (c=1.5 in chloroform).

2.5 g. Methyl 3β-acetoxy-12-oxo-18β-olean-30-oate are dissolved in 220 ml. glacial acetic acid to which are added a few drops of 40% solution of hydrogen bromide in acetic acid. 0.3 ml. bromine, dissolved in 13 ml. acetic acid, are added dropwise at ambient temperature to the solution. The solution is heated to 40° C. for 15 minutes and then left to stand at ambient temperature for 20 hours, whereafter the reaction mixture is poured on to ice and the precipitated solid is filtered off. Crystallization from methanol-methylene chloride gives 2 g. of colourless crystals of methyl 3β-acetoxy-12-oxo-18β-olean-9-en-30-oate; m.p. 288°-290° C.; $[α]_D^{25}$+93.6° (c=2 in chloroform).

2 g. Methyl 3β-acetoxy-12-oxo-18β-olean-9-en-30-oate are placed in an autoclave, together with a solution of sodium ethylate prepared from 15 ml. absolute ethanol and 1.7 g. sodium. The reaction mixture is heated under reflux in an atmosphere of nitrogen until complete dissolving is obtained and then 8 ml. 95% anhydrous hydrazine are added, followed by heating for 18 hours at 180° C. The reaction mixture is poured on to ice, acidified with hydrochloric acid and continuously extracted with chloroform. The evaporated chloroform extracts give a residue which is purified on a silica gel column, eluting with methylene chloride-methanol (96:4 v/v). 1.4 g. of crystalline 3β-hydroxy-18β-olean-9-en-30-oic acid is obtained; m.p. 312°-318° C. (with dec.); $[α]_D^{25}$+88° (c=0.2 in chloroform/methanol (9:1 v/v)).

EXAMPLE 2

3β-(3-Carboxypropionoxy)-18β-olean-9-en-30-oic acid.

A solution of 2.5 g. 3β-hydroxy-18β-olean-9-en-30-oic acid and 1.3 g. succinic anhydride in 10 ml. anhydrous pyridine is heated to 100° C. for 10 hours. The dark solution obtained is cooled to 30° C. and poured into 100 ml. of a 10% solution of ice-cold sulphuric acid. The precipitate formed is filtered off with suction, washed with 100 ml. of water preheated to 50° C. and dried in vacuo. 2.6 g. 3β-(3-Carboxypropionoxy)-18β-olean-9-en-30-oic acid are obtained which, after crystallisation from ethanol, melts at 314°–316° C. (with dec.); $[\alpha]_D^{25}+79.2°$ (c=0.2; chloroform/methanol (9:1 v/v)).

In an analogous manner but using acetic, propionic and glutaric anhydride instead of succinic anhydride, the following compounds are obtained:
3β-acetoxy-18β-olean-9-en-30-oic acid
3β-propionoxy-18β-olean-9-en-30-oic acid
3β-(4-carboxybutyroxy)-18β-olean-9-en-30-oic acid.

EXAMPLE 3

Disodium salt of 3β-(3-carboxypropionoxy)-18β-olean-9-en-30-oic acid.

To a suspension of 2 g. 3β-(3-carboxypropionoxy)-18β-olean-9-en-30-oic acid in 200 ml. water are added dropwise, with stirring, 7.2 ml. N aqueous sodium hydroxide solution. The solution is evaporated in vacuo at 20° C. and the residue is triturated with acetone and filtered with suction to give 2.1 g. of the disodium salt of 3β-(3-carboxypropionoxy)-18β-olean-9-en-30-oic acid; m.p. 320°–330° C. (with dec.); $[\alpha]_D^{25}+72.54$ (c=0.5 in 0.04N aqueous sodium carbonate solution/methanol (1:1 v/v))

In an analogous manner but using 3β-acetoxy-18β-olean-9-en-30-oic acid, 3β-propionoxy-18β-olean-9-en-30-oic acid and 3β(4-carboxybutyroxy)-18β-olean-9-en-30-oic acid as starting material, the following compounds are obtained: sodium salt of 3β-acetoxy-18β-olean-9-en-30-oic acid sodium salt of 3β-propionoxy-18β-olean-9-en-30-oic acid disodium salt of 3β-(4-carboxybutyroxy)-18β-olean-9-en-30-oic acid.

What we claim is:

1. The compound of the formula:

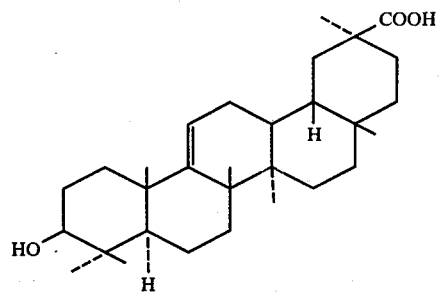

and the corresponding esters in the 3-position with mono- and di-alkanoic acids of 2 to 5 carbon atoms, as well as the pharmaceutically acceptable salts thereof with alkali metals, amino acids and copper.

2. 3β-Hydroxy-18β-olean-9-en-30-oic acid.
3. 3β-(3-Carboxypropionoxy)-18β-olean-9-en-30-oic acid.
4. 3β-Acetoxy-18β-olean-9-en-30-oic acid.
5. 3β-Propionoxy-18β-olean-9-en-30-oic acid.
6. 3β-(4-Carboxybutyroxy)-18β-olean-9-en-oic acid.
7. Disodium salt of 3β-(3-carboxypropionoxy)-18β-olean-9-en-30-oic acid.
8. Sodium salt of 3β-acetoxy-18β-olean-9-en-30-oic acid.
9. Sodium salt of 3β-propionoxy-18β-olean-9-en-30-oic acid.
10. Disodium salt of 3β-(4-carboxybutyroxy)-18β-olean-9-en-30-oic acid.
11. Pharmaceutical compositions, containing an ulcer inhibiting effective amount of at least one compound according to claim 1, in admixture with a solid or liquid pharmaceutical diluent or carrier.

* * * * *